United States Patent
Seward

(10) Patent No.: US 8,554,580 B2
(45) Date of Patent: Oct. 8, 2013

(54) AUTOMATED MANAGEMENT OF MEDICAL DATA USING EXPERT KNOWLEDGE AND APPLIED COMPLEXITY SCIENCE FOR RISK ASSESSMENT AND DIAGNOSES

(75) Inventor: James B. Seward, Rochester, MN (US)

(73) Assignee: General Electric Company, Schenectady, NY (US)

(*) Notice: Subject to any disclaimer, the term of this patent is extended or adjusted under 35 U.S.C. 154(b) by 399 days.

(21) Appl. No.: 12/578,325

(22) Filed: Oct. 13, 2009

(65) Prior Publication Data

US 2010/0094648 A1 Apr. 15, 2010

Related U.S. Application Data

(60) Provisional application No. 61/104,497, filed on Oct. 10, 2008.

(51) Int. Cl.
*G06Q 50/00* (2012.01)
(52) U.S. Cl.
USPC .................................. 705/3; 705/2; 600/300
(58) Field of Classification Search
USPC .......................................... 705/2–3; 600/300
See application file for complete search history.

(56) References Cited

U.S. PATENT DOCUMENTS

| | | |
|---|---|---|
| 4,945,476 A | 7/1990 | Bodick et al. |
| 5,272,625 A | 12/1993 | Nishihara et al. |
| 5,542,420 A | 8/1996 | Goldman et al. |
| 5,779,634 A | 7/1998 | Ema et al. |
| 5,924,074 A | 7/1999 | Evans |
| 6,154,750 A | 11/2000 | Roberge et al. |
| 6,381,611 B1 | 4/2002 | Roberge et al. |
| 6,801,916 B2 | 10/2004 | Roberge et al. |
| 6,915,254 B1 | 7/2005 | Heinze et al. |
| 7,087,018 B2 | 8/2006 | Comaniciu et al. |
| 7,155,447 B2 | 12/2006 | Roberge et al. |

(Continued)

FOREIGN PATENT DOCUMENTS

| | | |
|---|---|---|
| EP | 0973116 | 1/2000 |
| JP | 2002-059099 A | 2/2002 |

(Continued)

OTHER PUBLICATIONS

Barabási, Albert-László. *Linked: How Everything is Connected to Everything Else and What It Means for Business, Science, and Everyday Life.* New York: Penguin Group, 2002. pp. 1-8, 25-92, 109-122, 179-217.

(Continued)

*Primary Examiner* — Michelle Le
(74) *Attorney, Agent, or Firm* — Global Patent Operation

(57) ABSTRACT

A knowledgebase comprising a plurality of feature-sets is created using complexity science. The knowledgebase is accessible through a network to a computer, a system, and a computer program code that receives and analyzes medical data to determine the existence of a disease state. The medical data is input and correlated to features within the knowledgebase to identify feature-sets, each feature-set indicating a particular medical condition. After one or more feature-sets have been selected, associative algorithms consider the magnitudes or values of the medical data and, with the values of features in the feature-sets, assess the risk burden of the medical condition associated with the feature-set. An output is generated that may include diagnoses of one or more medical conditions, the risk burden of the medical condition(s), possible treatment options and prevention techniques.

9 Claims, 9 Drawing Sheets

(56) References Cited

U.S. PATENT DOCUMENTS

| | | |
|---|---|---|
| 7,244,230 B2 | 7/2007 | Duggirala et al. |
| 7,286,694 B2 | 10/2007 | Oosawa |
| 7,464,021 B1 | 12/2008 | Myers et al. |
| 7,599,534 B2 | 10/2009 | Krishnan |
| 7,640,051 B2 | 12/2009 | Krishnan et al. |
| 7,672,497 B2 | 3/2010 | Nicponski |
| 8,315,883 B2 | 11/2012 | Sakurai et al. |
| 2002/0128873 A1 | 9/2002 | Shimizu et al. |
| 2002/0198473 A1 | 12/2002 | Kumar et al. |
| 2004/0133083 A1* | 7/2004 | Comaniciu et al. ........... 600/301 |
| 2004/0158132 A1 | 8/2004 | Zaleski |
| 2004/0193022 A1 | 9/2004 | Torii et al. |
| 2004/0193036 A1 | 9/2004 | Zhou et al. |
| 2005/0021370 A1 | 1/2005 | Riff et al. |
| 2005/0137463 A1 | 6/2005 | Merkle |
| 2006/0058609 A1 | 3/2006 | Olstad |
| 2007/0033072 A1 | 2/2007 | Bildirici |
| 2007/0053567 A1 | 3/2007 | Adachi et al. |
| 2007/0083396 A1 | 4/2007 | Kanada et al. |
| 2007/0099219 A1 | 5/2007 | Teverovskiy et al. |
| 2007/0130511 A1 | 6/2007 | Roberge et al. |
| 2007/0239490 A1 | 10/2007 | Sullivan |
| 2009/0247872 A1 | 10/2009 | Rowlandson et al. |
| 2010/0217094 A1 | 8/2010 | Seward |

FOREIGN PATENT DOCUMENTS

| | | |
|---|---|---|
| JP | 2002-073816 A | 3/2002 |
| JP | 2004-288047 A | 10/2004 |
| JP | 2006-031190 A | 2/2006 |
| JP | 2008-077603 A | 4/2008 |
| WO | WO02/33577 | 4/2002 |

OTHER PUBLICATIONS

Cohen, Jack and Ian Stewart. *The Collapse of Chaos: Discovering Simplicity in a Complex World*. New York: Penguin Group, 1994. pp. 1-31, 178-218, 396-446.

Johnson, Neil F. *Simply Complexity: A Clear Guide to Complexity Theory*. Oxford: Oneworld, 2007. pp. IX-XIII, 3-66, 97-110.

May, Matthew E. *In Pursuit of Elegance: Why the Best Ideas Have Something Missing*. New York: Broadway Books, 2009. pp. 142-175.

Rogers, Mark. *Knowledge, Technological Catch-up and Economic Growth*. Cheltenham: Edward Elgar, 2003. pp. 146-151.

Cousins et al., "An Introduction to Predictive Modeling for Disease Management Risk Stratification," Disease Management, vol. 5, No. 3, 2002, pp. 157-167.

Bishop et al., "50 Years of Successful Predictive Modeling Should Be Enough: Lessons for Philosophy of Science," Philosophy of Science, vol. 69, Sep. 2002, pp. S197-S208.

Buehler et al., "Owning the Right Risks," Harvard Business Review, Sep. 2008, pp. 102-110.

Buehler et al., "The New Arsenal of Risk Management," Harvard Business Review, Sep. 2008, pp. 93-100.

Embi et al., "Biomedical Informatics and Outcomes Research: Enabling Knowledge-Driven Health Care," Circulation, vol. 120, 2009, pp. 2393-2399.

Fatema et al., "Increased Left Atrial Volume Index: A Potent Biomarker for First-Ever Ischemic Stroke," Mayo Clin Proc., vol. 83, No. 10, Oct. 2008, pp. 1107-1114.

Goldberger, "Non-linear dynamics for clinicians: chaos theory, fractals, and complexity at the bedside," Lancet 1996, vol. 347, 1996, pp. 1312-1314.

Grove et al., "Clinical Versus Mechanical Prediction: A Meta-Analysis," Psychological Assessment, vol. 12, No. 1, 2000, pp. 19-30.

Kawamoto et al., "Improving clinical practice using clinical decision support systems: a systematic review of trials to identify features critical to success," BMJ, Mar. 14, 2005, 8 pages total.

Lim et al., "A Comparison of Prediction Accuracy, Complexity, and Training Time of Thirty-Three Old and New Classification Algorithms," Machine Learning, vol. 40, 2000, pp. 203-228.

Plsek, et al., "The challenge of complexity in health care," BMJ, vol. 323, Sep. 15, 2001, pp. 625-628.

Ross et al., "Statistical Models and Patient Predictors of Readmission for Heart Failure: a Systematic Review," Arch Intern Med, vol. 168, No. 13, Jul. 14, 2008, pp. 1371-1386.

Wears et al., "Computer Technology and Clinical Work: Still Waiting for Godot," JAMA, vol. 293, No. 10, Mar. 9, 2005, pp. 1261-1263.

Wilson et al., "Complexity and clinical care," BMJ, vol. 323, Sep. 22, 2001, pp. 685-688.

"Studying Complexity Science," Complexity Science Focus, <http://www.complexity.ecs.soton.ac.uk>, accessed Oct. 15, 2008.

International Search Report issued in corresponding International Application No. PCT/US2009/060520, dated May 20, 2010 (3 pages).

Written Opinion of the International Searching Authority issued in corresponding International Application No. PCT/US2009/060520, dated May 20, 2010 (4 pages).

International Search Report issued in corresponding International Application No. PCT/US2010/025080 (U.S. Appl. No. 12/710,983 co-pending), dated Sep. 29, 2010 (3 pages).

Written Opinion of the International Searching Authority issued in corresponding International Application No. PCT/US2010/025080 (U.S. Appl. No. 12/710,983 co-pending), dated Sep. 29, 2010 (4 pages).

* cited by examiner

Fig. 6

| Portfolio/Disease | Ejection Fraction Systolis (pressure) | Filling Pressure E/e' (velocity) | Myocardial Relax e' (velocity) | LAVI (volume) | Atrial Fibrillation AF (unit) | Pulmonary Artery (pressure) | Superior Vena Cava Flow (velocity) | Blood Pressure (pressure) | Left Ventricle (mass) |
|---|---|---|---|---|---|---|---|---|---|
| Systolic disfunction | ABN | VAR | ABN | ABN | | | | | |
| Diastolic disfunction | VAR | VAR | ABN | ABN | | | | | |
| Athletic heart | NL | NL | NL | ABN | | | | | |
| Secondary AF | NL/VAR | VAR | ABN | ABN | X | | | | |
| Primary AF | NL | NL | NL | NL/VAR | X | | | | |
| Secondary Pul HTN | VAR | VAR | ABN | ABN | | <80 ABN | ABN | | |
| Primary Pul HTN | NL/VAR | VAR | VAR | NL | | ABN | ABN | | |
| Mixed Pulmonary HTN | VAR | VAR | ABN | ABN | | NL/VAR | ABN* | | |
| Parenchymal Pul Dis | NL | NL | NL | NL | | NL/VAR | ABN* | | |
| Atrial Volume Overload | VAR | NL | NL | ABN | | | | | |
| Atrial Pressure Overload | VAR | VAR | ABN | ABN | | | | | |
| Hypertension Heart Dis | VAR | VAR | ABN | VAR | | | | ABN | VAR |
| Constriction | | | ABN MEAN | ABN | | NL | | | |
| Restriction | | | ABN | ABN | | ABN | | | |
| HF with NL EF | NL | | ABN | ABN | | | | | |
| Shortness of Breath (Pul) | X | X | X | X | | X | X | | |
| Stress Test | X | X | X | X | | X | X | | |
| Heart Function | X | X | X | X | | X | X | | |
| Atrial Fibrillation | X | X | X | X | | | | | |
| Stroke | | | X | X | | | | | |

Fig. 7

| Portfolio/Disease Congenital Heart Disease | Right Ventricle /Right Atrium Size | Sub-costal | Apical 4-CH | TTE | TEE | Anom Pulmonary Vein | TV Displaced | Abdominal Aorta | Supra-sternal | Blood Pressure |
|---|---|---|---|---|---|---|---|---|---|---|
| Secundum ASD | ABN | YES | | YES | | | | | | |
| Sinus Venosis ASD | ABN | | | | YES | COMMON | | | | |
| Primum ASD | ABN | | YES | YES | | | | | | |
| Ebstein's Anom | ABN | | YES | YES | | | YES* | | | |
| Coarctation | | | | | | | | ABN | ABN | ABN |

Fig. 8

| Portfolio/Disease Valvular Heart Disease | Valve Area | Regurg Vol | Valve Morph | Gradient | e' | LAVI | E/e' | RV e' |
|---|---|---|---|---|---|---|---|---|
| Aortic Stenosis | X | | | X | X | X | X | |
| Aortic Regurgitation | | X | | | X | X | X | |
| Bicuspid | | X | X | X | X | X | X | |
| Mitral Stenosis | X | | | | X | X | X | |
| Mitral Regurg | | X | | | X | X | | |
| Pulmonary Stenosis | | | | X | | | | |
| Pulmonary Regurg | | | | | | | | |
| Tricuspid Stenosis | | | | X | | | | X |
| Tricuspid Regurg | | X | X | | | | | X |
| Carcinoid Valve Dis | | | X | | | | | X |

Fig. 9

| Portfolio/Disease Inconsistent Statements | LAVI | e' | EF | E/e' |
|---|---|---|---|---|
| ABN e' | NL | NL | | |
| > Age 60 | ABN | NL | | |
| Cardiomyopathy | | | | |

Fig. 10

| Portfolio/Disease | Lipid Profile | Fasting Glucose | Body Mass Index | Brain Naturetic Peptide | Immuno-globulins | Troponin | Ceruo-plasmin | Urine Copper | AST | LAVI |
|---|---|---|---|---|---|---|---|---|---|---|
| Metabolic Syndrome | ABN | ABN | ABN | | | | | | | |
| Amloidosis | | | | ABN | ABN | ABN | | | | |
| Wilson Disease | | | | | | | ABN | ABN | ABN | X |

AUTOMATED MANAGEMENT OF MEDICAL DATA USING EXPERT KNOWLEDGE AND APPLIED COMPLEXITY SCIENCE FOR RISK ASSESSMENT AND DIAGNOSES

FIELD OF THE INVENTION

This disclosure relates generally to the application of complexity science and expert knowledge to analyses of medical data for evaluation of risk for emergent diseases and diagnoses. More particularly, this disclosure relates to a method, a system, or a storage medium wherein medical data of a person is obtained, feature-sets of associated features of medical conditions are accessed from a medical knowledgebase, and values of the medical data are compared to ranges of values of the features of relevant feature-sets to identify any at-risk medical conditions of the person.

BACKGROUND

Diseases associated with age will reach pandemic proportions as the population both increases and ages simply because older humans are exposed to potential risk for longer periods of time. For instance, by 2020, age-associated cardiovascular disease alone will cause approximately 25 to 30 percent of all deaths in the world. Presently, treatment of age-associated diseases is predominately directed toward secondary management of observed clinical manifestations, risk factors, and associated adverse events. Risk factors are often considered consequences of underlying physiologic perturbations but these risk factors in and of themselves are not the primary cause of the disease manifestations ascribed to them. Risk factors are more likened to a consequence and not a cause.

Historically, patients have been assessed and managed on the basis of the presence or absence of these clinical risk factors and overt manifestations. By definition, risk factor management requires the patient to have a disease. The severity of the disease, moreover, may be indeterminate and an individual's response to therapy or the degree of preexisting disease burden is uncertain. This kind of risk management is not only user-unfriendly but in some instances is a disservice to the patient and the medical community. As an example, diabetes having a duration of one week most likely has a completely different risk burden than diabetes of 10 years' duration, so classification and treatment of these two disease states should be different and more importantly individualized.

Ideally, the choice of treatment of a disease should be based on the best evidence that comes from statistical research based on the measure of cause-related constituents. What we refer to as a disease is typically multivariable, comprises multiple and clustered risk factors, expresses variable or vacillating risk burdens, and demonstrates variable and/or indeterminate responses to therapy. A multivariable risk model is almost obligatory in order to assess a disease state because no single biomarker or feature is capable of measuring an individual's need for treatment or success in the prevention of adverse effects of the disease. The results of clinical trials are often used to predict the risk of disease with the ultimate goal leading to prevention of the disease in others. Clinical trials, however, typically follow a one-dimensional "top-down" approach with defined entry points, that is, the patient participating in the clinical trial has already passed a threshold which may be arbitrary and based on consensus. An "association" is frequently equated with cause-and-effect, however simply showing statistical independence or association is not adequate to demonstrate cause or clinical utility for risk prediction. The number of multivariable features of a disease interact with one another such that they not only change the interactions but, and this is more critical, the interaction may hide or erase their dependence on initial conditions. Another failure of clinical trials to evaluate risk factors to determine causation of a disease is that evaluation of multiple variables requires more complex analyses of all the factors necessitating a corresponding increase in the cohort size, often requiring hundreds or even thousands of patients. The averaging effects of these multitudes of patients in clinical trials, however, can give misleading results in the care of an actual individual having one or more of these multiple risk factors of variable duration and intensity. A "typical" patient does not fit the characteristics of an "average" patient so the clinical trials may actually contribute to over-treatment or under-treatment of the low- and high-risk patient groups.

Calculations of the long-term cost-effectiveness of treatment of risk factors are imprecise, and treatment recommendations are based principally on crude averages of disparate risk factors. Current management of risk factors certainly has benefits in terms of total number of years or quality-adjusted years gained, such as in the case of antihypertensive therapy. In general, however, the conventional approach to reporting overall results of clinical trials consigns the physician to an impoverished perspective in which risk data are flattened into a single effect: a therapy either works or doesn't. Treatment decisions are made easy because risk is fitted to the average patient and not real patients. No substantive clinical trials or cohort studies have defined risks, benefits, and costs of interventions on the basis of individual risk. As a result, existing guidelines for disease prevention have not achieved their objectives of controlling common risk factors.

Thus, the common practice of identification of complex multivariate clinical features and associated diseases might be interesting but does not address primary prevention of a disease. Primary prevention requires not only assessment of preclinical or emergent risk aggregates but also management of these risks before the disease expresses itself. Most diseases are consequences of an underlying physiological perturbations; thus risk assessment suited for primary prevention must have a different paradigm. Even though clinical trials recognize that disease states require analyses of many variables, conventional clinical risk algorithms have limited usefulness because the clinical risk factors studied may be poorly associated and do not have a numerical expression of disease intensity. Individual biomarkers or non-mathematical observations, moreover, may not be reproducible when attempting to predict emergent events. Indeed, management of a consequence does not ensure successful management of the cause. Without sufficiently addressing and quantifying both clinical and emergent risk burden of a disease state, treatment will be only partially successful for alleviating common diseases. Successful management of complex multivariate disease must transcend the limitations of the "one disease, one risk factor, and one seromarker" model and move medical science toward a more comprehensive and clinically realistic scenario.

Predictive modeling is one technique used to predict disease. In general, predictive modeling algorithms incorporate mathematical algorithms that interpret historical data and make predictions about the future. Predictive modeling, however, also has shortcomings especially when applied to prediction of disease. As mentioned above, the clinical models used to collect data involve people already having the disease and not the emergent risk embedded in the general public. Statistically speaking, the use of subjects having the disease is already a skewed population resulting in a collection of data points at an extreme side of the distribution, i.e., to the far left or the far right of the normal bell curve. It is known in the medical literature that multivariable risk models based on disparate observed risk factors and complex modifiers are difficult to assess. Further, it is a fact that individual risk and management predicated on clinical risk modifications or event incidences do not prevent the occurrence of the observed factors.

To further hinder the application of predictive modeling to disease states, most doctors are unaware of relevant results from evidence-based medicine studies, are overwhelmed by the diversity and magnitude of the medical literature or both. Advances in internet databases and information retrieval technology have spurred a new technology of analysis and dissemination of medical information to the decision makers. Telemedicine and super-crunchers, the current internet aids, and focus on diagnostic decision-support software are prompted by input of clinical findings. It is presumed that an internet search of the information embedded in the aggregate health care experience will enable a physician to make more informed diagnoses, decrease misdiagnosis and enhance the application of evidence-based medicine. These internet diagnostic software tools typically use a taxonomy of diseases to statistically search journal articles or working groups for word patterns most likely to be associated with the various diseases. Despite the best efforts and hopes, super information crunchers are currently applied in a top-down search for diagnoses and have been successful only about ten percent of the time. The paradigm is flawed from the beginning; merely finding data of a clinically apparent disease doesn't inform a patient or a doctor how to prevent the disease.

To move into a different paradigm of disease prevention and in the context of the embodiments described herein, it becomes useful to discuss the differences between data, metadata, understanding, and knowledge. Data are numbers derived from observation, mathematical calculation or experiments, and are typically acquired using a machine. Information is data in context; information is a collection of data and associated explanations, interpretations or discussions concerning a particular object, event or process, e.g., a diagnostician's interpretation of data's relationship to normal or abnormal states. Metadata is data about data and describes the context in which the information was obtained or is used, e.g., summaries and high-level interpretation of data such as a "final report". Understanding is the use of metadata and information to make logical choices, e.g., a doctor selects features or tests when considering a particular disease and/or patient. Understanding is also considered the human capacity to render experience intelligible by relating specific knowledge to broad concepts. Knowledge is a combination of metadata and an awareness of the context in which metadata can be successfully applied, e.g., the relationships between features. In artificial intelligence, knowledge determines how to use and relate information and metadata. Accumulated knowledge when applied to artificial intelligence algorithms is commonly referred to as a knowledgebase 140. In general, a knowledgebase 140 is a centralized repository of information and knowledge. Each knowledgebase 140 is unique to the expert or experts from which it emanates but an undisciplined knowledgebase 140 is incapable of yielding high order prediction. Clinical medicine has explored use of diverse forms of information science for determination of wellness and management of disease but so far implementation of these technologies has not successfully replicated or replaced the complex multivariable knowledgebase 140 of the medical providers having associative knowledge of the disease constituents, e.g., physicians, specialists and technologists. So far, the use of artificial intelligence per se in clinical medicine remains illusive and unattainable.

Informatics includes the general science of information, the practice of information processing and engineering of information systems. Informatics is the study of the structure, behavior and interaction of natural and artificial systems that store, process and communicate information. Health and medical informatics deals with the resources, devices and methods required to optimize the acquisition, storage, retrieval and use of information in health and biomedicine. On the other hand, information science, of which complexity science is included, is an interdisciplinary science of the collection, classification, manipulation, reporting, storage, retrieval and dissemination of information. Information science and informatics are thus very similar, with information science generally being considered a branch of computer science and informatics is a more closely related to the cognitive and social sciences.

Complexity science is an emerging study wherein scientists often seek simple non-linear coupling rules that result in complex phenomena. Human societies, human brains are examples of complex systems in which neither the components nor the couplings are simple or linear. Nevertheless, they exhibit many of the hallmarks of complex systems. Although biological systems are typically nonlinear, nonlinearity is not a necessary feature of complex systems modeling: useful macro-analyses of unstable equilibrium and evolution processes of certain biological/social/economic systems can be carried out also by sets of linear equations, which do nevertheless entail reciprocal associative dependence between variable parameters. Of particular import here, disease can be studied as a complex system. In complexity science numerical expressions of natural laws are called features. A feature is considered a characteristic if it permits recognition of an event. For instance, one person recognizes another person by such features as sex, skin, eyes, height, etc. In complexity science, these features are assembled into small sets, called feature-sets, of highly associated features that reinforce prediction. Each successive encounter of the "stranger" reinforces the small feature-set. Disparate features and less connected features such as skin temperature and clothing are not particularly helpful in assuring repeated recognition.

Confident prediction of subclinical or pre-emergent disease is essential to prediction and prevention of disease and management of the current medical crisis but current disease prediction and management are insufficient. There are numerous sources of relevant medical data derived from various state-of-the-art medical technologies where data are typically expressed as numerical variables related to normal or abnormal states. Application of data informatics and information science which are intended to assist in predicting or directing medical care have met limited clinical utility in the management of human disease. Such information solutions include: telemedicine, clinical trials, clinical risk scores, binary gaming algorithms, super-crunchers, etc. True artificial intelligence remains and will remain impractical for a few more decades. However, in the context of information science, complexity science is a powerful predictor of disease and determiner of the magnitude of that risk, as described herein. Complexity science has been used in medicine in a comparison of prediction accuracy, complexity and training time of classification algorithms. There are published articles on the application of nonlinear and linear dynamics: chaos theory, fractals and complexity for physicians at the bedside. Complexity science has been principally applied to poorly-connected disparate features of a clinical setting. Complexity science has also been more commonly applied to the social sciences.

The medical community has yet to identify and embrace a feature-set of risk models, also called disease surrogates, which are capable of detecting disease in its formative or pre-emergent stages. Identification and individual characterization of asymptomatic subjects in the general population who carry a high risk remains problematic and inadequate. To date, no satisfactory solution to this dilemma has been adopted.

BRIEF SUMMARY

The present disclosure is directed to a method, a system which incorporates aspects of the method, a non-transitory computer-readable storage medium which incorporates aspects of the method in executable program steps, and a medical knowledgebase created to be an integral part of such method, system and storage medium.

Particularly the method evaluates medical data of a person to identify, if any, at-risk medical conditions. The method begins by obtaining the medical data, wherein it has features of at least one of various medical conditions and such that at least some of the features have values. A medical knowledge base is accessed. The knowledge base has a plurality of feature-sets relating to various medical conditions. Each of the plurality of feature-sets has a group of highly-associated features relating to particular ones of the various medical conditions. At least some of the highly-associated features have ranges of values. A subset of the plurality of feature-sets is determined by correlating at least two of the features of the medical data with at least two of the highly-associated features of the feature-sets in the subset. In this way, knowledge of the features of the medical data is transformed to metadata in the form of the group of transformed highly-associated features of each of the feature-sets in the subset. Features of the medical data are then compared such that a normal or abnormal characteristic or magnitudes of values of the medical data are compared with similar characteristics and ranges of values of the transformed highly-associated features with respect to normality. The comparison is interpreted relative to a standard so as to identify any at-risk medical condition.

With respect to a medical knowledge base, a method is provided for adding or modifying a candidate feature-set relating to a medical condition to the knowledge base. A candidate feature is considered the candidate feature-set. The candidate feature-set has at least one other existing feature. The candidate feature is compared with the at least one other existing feature. The candidate feature is selected for inclusion in the candidate feature-set if when the at least one candidate feature is one of abnormal and within a range of values which are abnormal, there is a correlative effect with the at least one other existing feature such that together they have an increased association level with the medical condition to which the candidate feature-set relates.

BRIEF DESCRIPTION OF THE DRAWINGS

FIGS. 6-10 are examples of embodiments of feature-sets with respect to various medical conditions;

DETAILED DESCRIPTION

Figure 1:
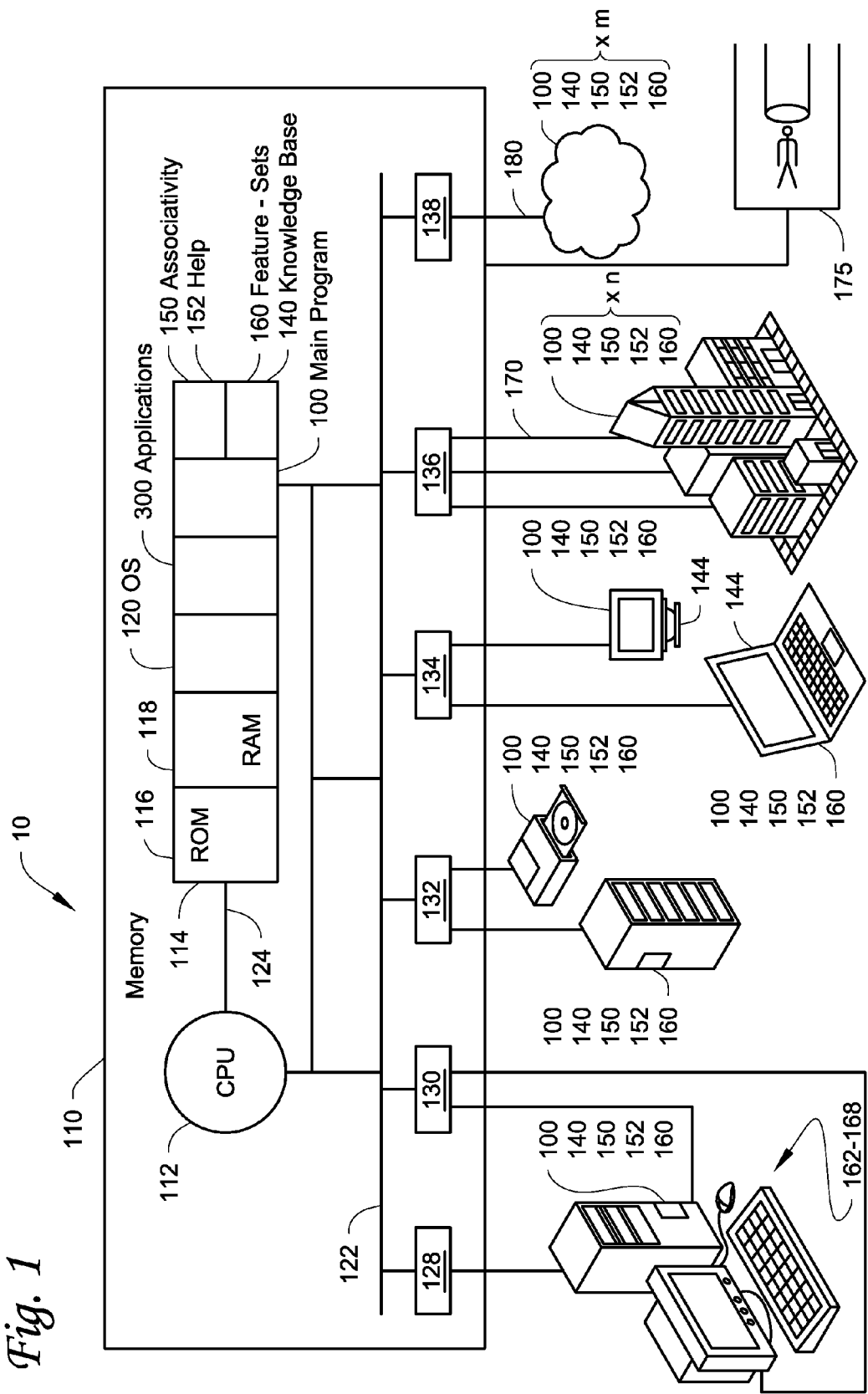
FIG. 1 is a block diagram of a computer system and a network in accordance with an embodiment.

The description includes reference to the accompanying drawings. The invention may be embodied in many different forms and should not be construed as limited to the embodiments set forth herein. Rather the illustrated embodiments are provided so that this disclosure is thorough and complete, and fully conveys the scope of the invention to those skilled in the art. Like numbers refer to like elements throughout.

As will be appreciated by one of skill in the art, the embodiments described herein are a method, a data processing system, a computer program product and a service that maintain a knowledgebase 140, a plurality of associative algorithms 150 and a plurality of feature-sets 160 each having a set of highly-associated features that identify a medical condition and that apply one or more associative algorithms that are applied to evaluate the input medical data representing the magnitude of the features, wherein an individual's risk of a medical condition or disease is identified and determined. Determining the individual's risk of a medical condition or disease includes quantifying a physiologic variance from normal. Accordingly, components of the embodiments may take the form of a hardware aspect or an embodiment combining software and hardware aspects. Furthermore, components of the embodiments may take the form of a computer program product on a computer-usable storage medium having computer-usable code embodied in the medium. Any suitable computer readable medium may be utilized including solid-state storage devices, hard disks, CD-ROMs, optical storage devices, portable memory, a transmission media such as those supporting the Internet or an intranet, or magnetic storage devices.

Computer program source code of the software components that maintain a knowledgebase 140, a plurality of associative algorithms 150 and a plurality of feature-sets 160 as described herein may be written in an object-oriented programming language such as C, Java, Smalltalk or C++. Object code of the components comprising the knowledgebase 140, a plurality of associative algorithms 150 and a plurality of feature-sets 160 may execute entirely on an individual server or client, partly on an individual or a backup server or client, partly on the individual or backup server or client and partly on a remote server or client or entirely on the remote server or client. In the latter scenario, the remote server or client may be connected to the individual or backup server or client through a local area network (LAN) or a wide area network (WAN), or the connection may be made to the remote server or client via the Internet using an Internet Service Provider.

The methods to maintain a knowledgebase 140, a plurality of associative algorithms 150 and a plurality of feature-sets 160 as described herein are described below with reference to flowchart illustrations and/or block diagrams of methods, apparatus (systems), components, and computer program products according to the embodiments. It will be understood that each block of the flowchart illustrations and/or block diagrams, and combinations of blocks in the flowchart illustrations and/or block diagrams, can be implemented by computer program instructions. These computer program instructions may be provided as one or more components to a processor of a general purpose computer, special purpose computer, or other programmable data processing apparatus to produce a machine, such that the components, which execute via the processor of the computer or other programmable data processing apparatus, create means for implementing the functions/acts specified in the flowchart and/or block diagram block or blocks.

These computer program components of the knowledgebase 140, a plurality of associative algorithms 150 and a plurality of feature-sets 160 as described herein, as well as the user and application interfaces necessary to implement them may also be stored in a computer-readable memory that can direct a computer or other programmable data processing apparatus to function in a particular manner, such that the components stored in the computer-readable memory produce an article of manufacture including components which implement the function/act specified in the flowchart and/or block diagram block or blocks. The computer program components may be loaded onto a computer or other programmable data processing apparatus to cause a series of operational steps to be performed on the computer or other programmable apparatus to produce a computer implemented process such that the components which execute on the computer or other programmable apparatus provide steps for implementing the functions/acts specified in the flowchart and/or block diagram block or blocks.

Referring to FIG. 1, a high-level block diagram of a computer network system 10 consistent with embodiments described herein to maintain a knowledgebase 140, a plurality of associative algorithms 150 and a plurality of feature-sets 160 as well as the user and application program interfaces necessary to implement them as described herein is shown. Computer network system 10 preferably comprises a number of networked computers 110, each of which may have a central processing unit (CPU) 112, memory 114, and various digital and/or analog interfaces 128-138. The various devices communicate with each other via an internal communications bus 122. CPU 112 is a general-purpose programmable processor, executing instructions stored in memory 114; while a single CPU 112 is shown in FIG. 1, it should be understood that computer systems having multiple CPUs could be used. CPU 112 is capable of executing an operating system 120 and the process and method steps and the computer program product that that maintains a knowledgebase 140, a plurality of associative algorithms 150 and a plurality of feature-sets 160 as described herein and other applications 300. CPU 112 is also capable of generating the computer program components that maintain a knowledgebase 140, a plurality of associative algorithms 150 and a plurality of feature-sets 160 and the appropriate user and application program interfaces as described herein and is capable of receiving and transmitting the program instructions embodying the methodology for performing these processes, functions and methods 100 described herein. Communications bus 122 supports transfer of data, commands and other information between different devices, and while shown in simplified form as a single bus, it is typically structured as multiple buses including an internal bus 124 which may connect the CPU 112 directly with memory 114.

Memory 114 comprises a read only memory (ROM) 116 and a random-access memory (RAM) 128 for storing the operating system 120, the components that maintain a knowledgebase 140, a plurality of associative algorithms 150 and a plurality of feature-sets 160 as described herein, and other applications 300, data and programs. Typically, those portions or programs, routines, modules of the operating system 120 necessary to "boot up" are stored in ROM 116. RAM 118 typically stores programs and data that will be erased when the computer turns off. Memory 114 is shown conceptually as a single monolithic entity but it is well known that memory is often arranged in a hierarchy of caches and other memory devices, some or all of which may be integrated into the same semiconductor substrate as the CPU 112. RAM 118 devices comprises the main storage of the computer, as well as any supplemental levels of memory, e.g., cache memories, non-volatile or backup memories, programmable or flash memories, portable memories, other read-only memories, etc. In addition, memory 114 may be considered to include memory storage physically located elsewhere in the computer, e.g., a cache memory in a processor or other storage capacity used as a virtual memory, e.g., as stored on a mass storage device or on another computer coupled to the computer via network. It is fully realizable that the components that maintain and include the knowledgebase 140, a plurality of associative algorithms 150 and a plurality of feature-sets 160 as described herein can be used to access data from its source and/or access a distributed knowledgebase 140 within any memory 114 including ROM and RAM located within and outside the computer processing device 110 upon which the components that maintain a knowledgebase 140, a plurality of associative algorithms 150 and a plurality of feature-sets 160 as described herein are installed and executing. As shown in FIG. 1, components that maintain and embody a knowledgebase 140, a plurality of associative algorithms 150 and a plurality of feature-sets 160 as described herein may be connected to like components stored on other devices across the network and may acquire medical data or otherwise exchange analog and digital data to implement and execute the methods in accordance with the principles herein.

Operating system 120 and the components that maintain a knowledgebase 140, a plurality of associative algorithms 150 and a plurality of feature-sets 160 as described herein and other applications 300 reside in memory 114. Operating system 120 provides, inter alia, functions such as device interfaces, management of memory pages, management of multiple tasks, etc. as is known in the art. Examples of such operating systems may include Linux, Aix, Unix, Windows-based, Z/os, V/os, OS/400, an Rtos, a handheld operating system, etc. These operating systems 120 and other various of the components that maintain and embody a knowledgebase 140, a plurality of associative algorithms 150 and a plurality of feature-sets 160 as described herein and other applications 300, other components, programs, objects, modules, etc. may also execute on one or more processors in another computer coupled to computer 110 via a network 170, 180, e.g., in a distributed or client-server computing environment, whereby the processing required to implement the functions of a computer program may be allocated to multiple computers 110 over a network 170, 180.

In general, the components that maintain and embody a knowledgebase 140, a plurality of associative algorithms 150 and a plurality of feature-sets 160 as described herein execute within the CPU 112 to implement the embodiments, whether implemented as part of an operating system or a specific application, component, program, object, module or sequence of instructions may be referred to herein as computer programs or simply components. The components that maintain and embody a knowledgebase 140, a plurality of associative algorithms 150 and a plurality of feature-sets 160 as described herein typically comprise one or more instructions that are resident at various times in various memory 114 and storage in a device and that, when read and executed by one or more processors in the processing device 110, cause that device 110 to perform the steps necessary to execute steps or elements embodying the various aspects described. The components 100 comprise at least one or more knowledgebases 140. The components 100 further comprise one or more feature-sets 160 of highly-associated features that characterize a medical condition or disease or a risk of the medical condition or disease in accordance with the features described herein. Components 100 further comprise one or more associative and evaluative algorithms 150 that acquire and evaluate input medical data of the features in a feature-set to determine an individual's risk for the medical condition or disease. Components 100 further comprise data acquisition and input and data sorting methods, and output components that display the results in a format through an application or user interface accessible by a physician or other user, as well as other appropriate user and application program interfaces.

It should be appreciated that computer 110 typically includes suitable analog and/or digital interfaces 128-138 between CPU 112 and the attached devices as is known in the art. For instance, computer 110 typically receives a number of inputs and outputs for communicating information externally. For interface with a physician or other user, computer 110 typically includes one or more software developer input devices 162-168, e.g., a keyboard, a mouse, a trackball, a joystick, a touchpad, and/or a microphone, among others, and a display such as a CRT monitor, an LCD display panel, and/or a speaker, among others. It should be appreciated, however, that some implementations of computer 110, e.g., some server implementations, might not support direct software developer input and output. Terminal interface 134 may support the attachment of single or multiple terminals or laptop computers 144 and may be implemented as one or multiple electronic circuit cards or other units. It is envisaged that input from one or more medical tools 175 be directly connected, e.g., data from sonography, tomography, laboratory testing, electrocardiography, etc. so that medical data can be directly input into computer system 110. It is understood that medical data can also be input via portable memory, over a transmission medium such as the Internet, telephone or a wireless, or even entered manually. Further medical data can be accessed from data storage preferably comprising one or more rotating magnetic hard disk drive units, although other types of data storage, including a tape, flash memory or optical driver, could be used. For additional storage, computer 110 may also include memory 114 comprising one or more mass storage devices, e.g., a floppy or other removable disk drive, a hard disk drive, a direct access storage device (DASD), an optical drive e.g., a compact disk (CD) drive, a digital video disk (DVD) drive, etc., and/or a tape drive, among others. The knowledgebase 140, one or more feature-sets 160, and/or one or more associative algorithms 150 may be located on storage, including RAMs or mass storage devices of different computers 110 that are located through the Internet 180, a WAN 170, and other connected machines 128. One of skill in the art will further anticipate that the interfaces 128-238 may also be wireless.

Furthermore, computer 110 may include an interface 136, 138 with one or more networks 170, 180 to permit the communication of information with other processing devices and knowledgebase(s) 140 coupled to the network(s) 170, 180. Network interface(s) 136, 138 provides a physical and/or wireless connection for transmission of data to and from a network(s) 170, 180. Network(s) 170, 180 may be the Internet, as well as any smaller self-contained network such as an Intranet, a wide area network (WAN), a local area network (LAN), or other internal or external network using, e.g., telephone transmissions lines, satellites, fiber optics, T1 lines, wireless, public cable, etc. and any of various available technologies. One of ordinary skill in the art understands that computer system 10 may be connected to more than one network 170, 180 simultaneously. Computer system and remote systems 128 may be desktop or personal computers, workstations, a minicomputer, a midrange computer, a mainframe computer. Any number of computers, processing devices of various medical testing and data acquisition apparati, other microprocessor devices, such as personal handheld computers, personal digital assistants, wireless telephones, etc., which may not necessarily have full information handling capacity as the large mainframe servers, may also be networked through network(s) 170, 180. Still yet, the embodiments may include any of the components of the methods and program products to be deployed, managed, serviced by a service provider who offers to perform one or more of: generate or modify one or more knowledgebases 140, provide input medical and clinical data of the features of a feature-set, generate, provide or modify any of the associative algorithms or other process steps that the components 100 or its other components can perform.

In the context herein memory 114 may also be considered nonvolatile or backup memories or a programmable or flash memories, read-only memories, etc., in a device physically located on a different computer, client, server, or other hardware memory device, such as a mass storage device or on another computer coupled to computer via network. Memory 114 may comprise remote archival memory such as one or more rotating magnetic hard disk drive units, a tape or optical driver having any of the components herein. Memory 114 may also be considered one or more mass storage devices, such as a floppy or other removable disk drive, a hard disk drive, a direct access storage device (DASD), an optical drive e.g., a compact disk (CD) drive, a digital video disk (DVD) drive, etc., and/or a tape drive, among others, each of which may have one or more components described herein.

The embodiments described herein apply a "bottom-up" approach to predicting and evaluating the risk or variance from normal of a medical condition where investigators search for clues in physical, functional, chemical, and/or biological phenomena to deduce an underlying theory or course of action. The objective is to ascertain what observable phenomena are fundamental and then to connect these fundamental phenomena as features of risk of a medical condition or disease or the disease itself. In this model, features are mathematical or verbal data determined by natural rules. In other words, features are mathematical or logical data derived from tests, examinations, machines, etc. As explained in the background, instances of a disease or risk are complex expressions of normal or abnormal states and emerge from a collection of interacting features. The "bottom-up" approach applied herein provides a multivariate feature-stratified risk analysis and compares the effect across a fuller spectrum of baseline risk than does the "top-down" analysis. The particular appeal of the bottom-up model is the potential for using interrelated quantifiable features to detect subclinical or pre-emergent disease states, predict future health events, and prevent expression of the disease. Current use of the bottom-up approach to disease characterization and management is very limited.

Figure 2:
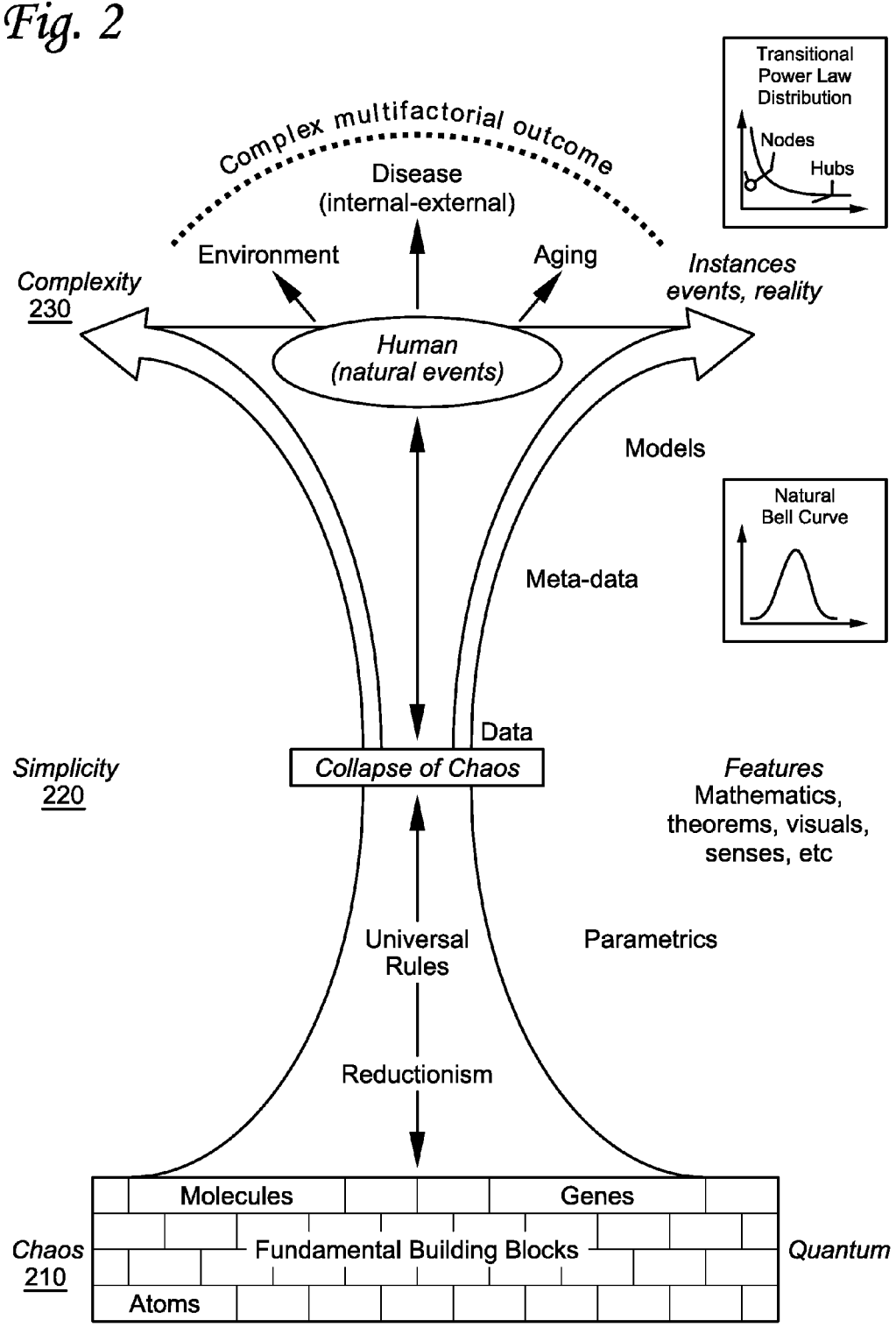
FIG. 2 is a schematic illustration of using complexity signs with respect to an embodiment.
Figure 11:
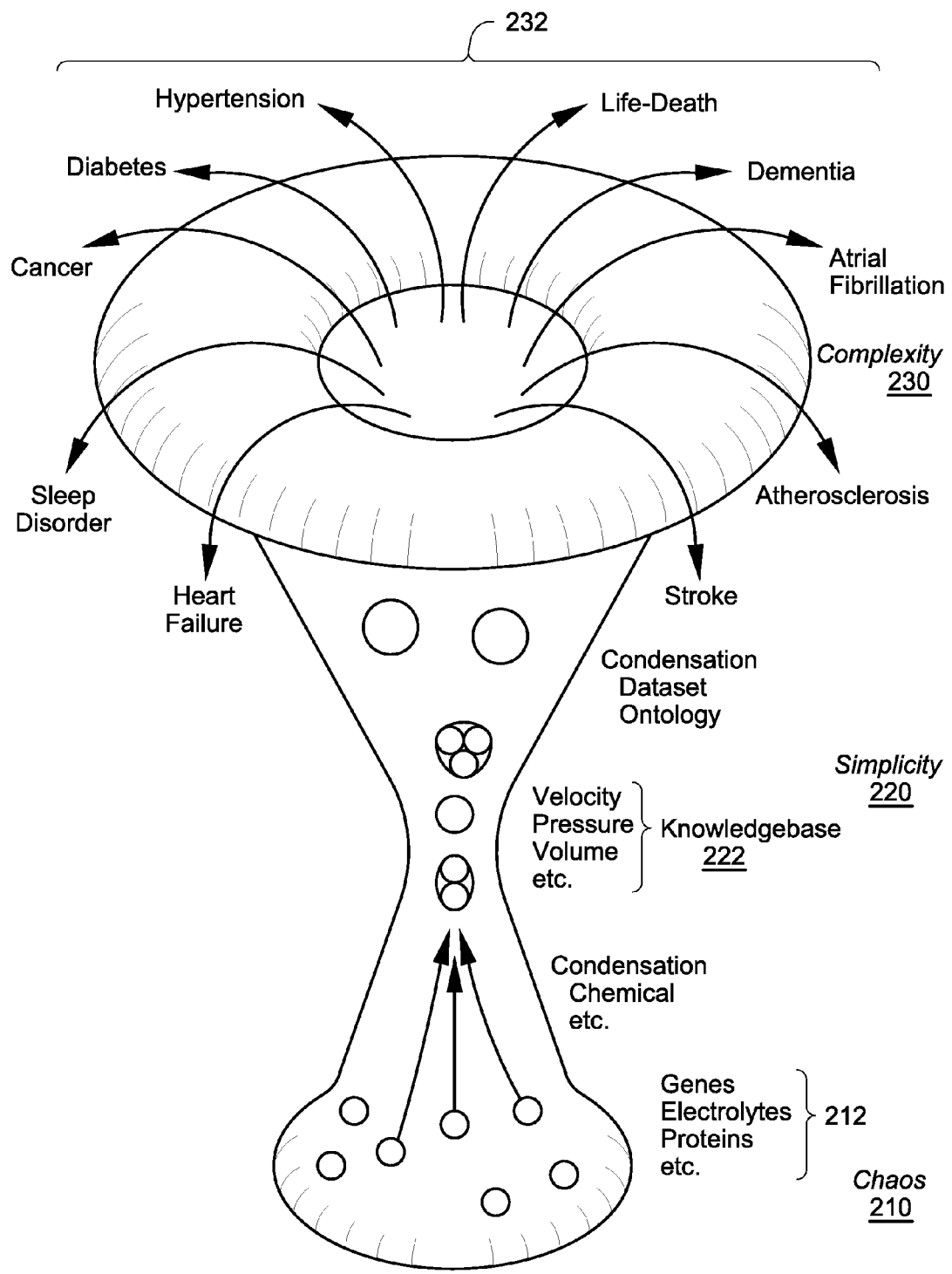
FIG. 11 is a schematic illustration of using complexity signs with respect to an embodiment.

The science of complexity as embodied in the knowledgebase 140 and associative algorithms 150 herein for the study of disease or predisease instances that emerge from feature-sets of closely associated features actually has greater accuracy in the prediction of emergent instances or risk assessment. Some of the motivating paradigms for the embodiments described herein are that "[s]ystems that have the same deep similarities must obey the same simple rules" and that "every scientist should be trying to see the world in the simplest possible way." Simple but deep natural laws govern the structure and evolution of all complex networks, including human disease. Each risk assessment technique has its own limitations and advantages but the information sciences and in particular, complexity science has logical appeal. Complexity science is the study of the phenomena that emerge from a collection of closely associated features, which in medicine best relates to an expressed disease or risk. Consider FIGS. 2 and 11, which are graphical representations of systems from a perspective of complexity science. At the bottom of FIGS. 2 and 11, there is chaos 210 which represents the fundamental constituents of the system without organization. FIG. 11 shows that in the world of medicine, these fundamental constituents 212 include genes, proteins, sugars, electrolytes, molecules, atoms, etc. Amid these fundamental constituents 212 are naturally abiding and consistent laws of nature that cause these constituents 212 to order themselves into systems, states, networks, etc. This phenomenon is called deterministic chaos. Organized states such as disease incidences would not be able to evolve without the existence of these rules or patterns of nature. At the top order of complexity 230 and opposite chaos are fractals; a fractal is a pattern that repeats within itself so a system of fractals represents high organization. In between chaos 210 and complexity 230 or fractals is simplicity 220. Complexity science concerns itself with the study of simplicity groupings leading to complex systems of fractals. FIG. 11 shows an example of simplicity groupings as a knowledgebase 222 including features of velocity, pressure, and volume. In the context described herein, complexity science is applied to simplify and ascertain a small number of highly associated quantifiable features to characterize an existing or pre-emergent medical condition and disease state.

When attempting to predict and quantify the risk of a medical condition or to prevent, treat, or cure a disease, physicians face immense challenges when they disregard the complex interconnectedness of living matter and focus on the chaos, i.e., the specific molecules or genes or clinical risk factors. The consideration of the disease features within the context of complexity science simplifies the complexities and provides a framework to consider the unpredictability of the interaction of fundamental constituents. The consequence of this framework allows for the anticipation of one or more complex events, examples shown in FIG. 11 as disease states 232, such as cancer, diabetes, life-death, dementia, atrial fibrillation, atherosclerosis, stroke, heart failure, sleep disorder, and hypertension. Anticipation leads to prediction of a medical condition such as a disease state 232, enabling physicians to rapidly respond to the risk of possible disease states 232 with preventative tactics so that the full expression of the disease state 232 may be avoided.

Diseases and/or risk of diseases have most or all of the following characteristics: (1) a collection of many interacting features that are closely related to each other, are members of a group, or share some common information; (2) the features' behavior is affected by a feedback system in which something happening at one time or place affects what is happening at another; (3) the features can adapt in accordance with improving its performance; and (4) the system is typically "open" and can be influenced by its environment. Compare these disease or risk attributes with complex multivariable systems that show the following behaviors: (1) the complex system appears alive, evolving in a nontrivial and complicated manner under the influence of feedback; and (2) the complex system has instances that unexpectedly emerge in terms of when they arise and cannot usually be predicted based on knowledge of an individual feature such as a particular molecule, gene, or computation; (3) complex systems exhibit complicated phenomena that typically arise in the absence of any central controller, in other words, the complex system is more than the sum of its parts; and (4) the complex system shows a mix of ordered and disordered behavior that can move between order and disorder on its own, and seemingly shows pockets of order, e.g., symptomatic heart failure can have a variable or vacillating normal or abnormal associated features. The embodiments described herein take advantage of the inventor's recognition of the applicability of complexity science to analyses of pre-emergent and existing disease states.

Estimating the risk of clinical diseases is imprecise at best but additional use of biomarkers, e.g., echo/Doppler, biochemical tests, radiography, etc. improves the quantification of an individual's risk burden. Tailoring risk reduction to a person's risk burden is appealing. To be accepted by the medical and scientific community, the observed physiological phenomena or biomarkers to be selected as features must meet at least one and preferably most of several specific criteria: (1) be a reproducible measure that adds to the prognostic value beyond conventional risk factor association; (2) have incremental value with regard to specificity and sensitivity in population studies; (3) create a new treatment assessment or reclassification and prevention or reduce misclassification thereby avoiding inappropriate treatment; (4) be easily obtainable and reproducible with a low false-positive rate; (5) have the prospect for substantially improving outcome and relative risk prediction; and (6) measure therapeutic success with a substantial decrease in adverse events. Based on feature-sets of quantifiable morphologic and physiologic features, the Echo/Doppler model is one example of an ideal biomarker. A challenge is recognizing and validating which specific features determine the stability of a complex emergent disease.

In normal states, natural physiologic features typically follow bell curves having correlations that decay rapidly obeying exponential laws. If a system, however, undergoes a phase transition, e.g., transition of water from liquid to solid, a state of order to disorder, or a transition of chaotic biochemicals to a disease state, powerful laws of self-organization called power laws characterize that transition. A power law distribution is not bell shaped but rather is a histogram following a continuously decreasing curve thereby implying that many small events or nodes coexist with a few large events or hubs. Power law distribution of a scale-free network predicts that most associations have only a few links but are held together by a few highly connected hubs, similar to an air traffic system. Large numbers of poorly connected associations or nodes decay to a few dominant features or hubs that are more closely related to cause-and-effect and the stability of the network. It is worthwhile to note that in natural networks, failures predominantly affect the smaller more numerous associations but these weak associations actually contribute little to the network's integrity.

Embodiments of predictors of pre-emerging disease states, as described herein, use "computed intelligence" based on the science of complexity. In contrast to the conventional medical information systems of trials, super-crunchers, clinical risk scores that typically use disparate clinical and technology derived data, human experts choose and validate which medical data is relevant and further choose which features to include in a feature set of that medical condition. The integrated probability of many experts' knowledge defines feature-selection and relationships among the features. By way of example only, although echo/Doppler and other state-of-the-art data acquisition technologies are examples of preferred means of characterizing and quantifying features, they have received little attention as components of treatment algorithms. Instead, individual and small grouping of disparate seromarkers and clinical risk factors have been the classic means of formulating risk and treatment algorithms.

When considering a particular medical condition or disease as a network, conventional treatment of a complex disease focuses on poorly connected features and has limited effect on the emergence of additional disease or complications. Just because disease is complicated and multivariate doesn't mean it has to arise from a complicated or complex set of rules. Recall that in FIG. 2, complexity science encourages us to seek simplicity within apparently complex states, and as applied to medicine teaches us to characterize, manage, and prevent disease using a small number of highly connected features. Multivariate disease states are in fact the consequence of relatively simple rules operating one level below complex. Features determined by natural rules may include, e.g., a percentage of the heart's filling pressure [mm Hg], myocardial relaxation [cm/s], central aortic pressure [mm Hg], and many others. Complex diseases cannot be managed and prevented unless multiple of the highly connected features are disabled simultaneously at which time the disease will collapse. Understanding and applying the power law distribution of naturally-occurring networks to disease systems requires the demise of the paradigm that a molecule, seromarker or individual pieces characterizes the disease. Instead, small feature-sets of extraordinarily interconnected features carry most of the action and signify self-organization in complex human disease.

According to complexity science, the hubs organized into feature-sets of a network (wherein a feature-set is a set of closely-associated dominant features), define the network's topology and determine the structural stability, dynamic behavior, robustness, and error and attack tolerance of the network. Risk or disease intensity evaluation for prediction of a disease is dependent on the small number of most highly connected features. A feature-set of simple but highly connected features defines emergent disease and predicts risk thereby allowing the predictions to focus treatment and monitor success or failure. Focused identification and management of a small feature-set of highly selected features can be used to detect and manage emergent disease risk and propel medical care toward an era of prevention. That is, treatment of the dominant features in a feature-set has the same effect as treatment of the pre-emergent or existing disease itself!

A highly interconnected network of interacting features is the key to predicting complex events. Pre-emergent or existing disease states are complex events, so when applied to medicine, complexity science facilitates an understanding of prediction and control of emergent disease and risk associated with that disease. The first step is to create a knowledgebase 140 of features and defined feature-sets 150, each feature within a feature-set 150 having an ascertainable and measurable value and that is associated with the occurrence of a medical condition or a disease. The knowledgebase 140 catalogs and validates morphologic, physiologic and biologic data as features, characterizes natural physiological events and establishes the feature-sets of features matched to specific diseases and/or specific or general risks. Preferably, this knowledgebase 140 is dynamic and represents a network of physiologic and morphologic changes assembled one feature at a time with each additional feature preferentially connecting to an existing feature. Medical data are preferably treated as quantifiable features and as variables of mathematical functions that account for normal vacillation of natural physiological events. Variance from "normal" or transition from one state to another may be expressed as a numerical averaging of the features contained within the feature-set. Adopting the nomenclature of complexity science to the description herein: a node is defined as a collection of common but less-connected features; a hub or feature-set is defined as a collection of few dominate features that are strongly-associated with each other and with an emergent (preclinical) disease. Networks of nodes and hubs sustain basic functions of a network, including the transition to a disease state. Each feature-set is a small collection of hubs comprising the most strongly associated features characterizing a medical condition or disease state. Data from an acquisition technology is either directly input, as in a sonogram or x-ray, or indirectly through a semiconductor memory or entered manually by a person, to a knowledgebase 140. After creation of the knowledgebase 140, it is stored with and as a plurality of features and derived feature-sets 160.

The knowledgebase 140 is preferably accessible to experts to select features within specific feature-sets. The knowledgebase 140 is also preferably an open-source living collection of expert knowledge that is subject to constant peer review and revision, whereby experts can edit, add, delete, comment and refine the feature-sets having a small number, e.g., preferably two to four, but generally less than ten, highly-associated features associated with a medical condition or disease state. The addition of less important features (i.e. nodes or data) to an efficient highly selected feature-set does not substantially affect the power of prediction. This finding is characteristic of a scale-free network where the addition or elimination of less connected nodes will not appreciably affect the integrity of the network. For comparison, WIKIPEDIA is an online database wherein nearly anyone may contribute to the information contained therein. The knowledgebase 140 according to the description herein contains knowledge, not merely data (i.e. Knowledge is a combination of metadata and an awareness of the context in which metadata can be successfully applied). Further, the embodiments herein include the knowledgebase 140 being peer-reviewed. Even further, the embodiments herein include expert knowledge being included in the knowledgebase 140, wherein only the experts may be the contributors. Additional features can be added or subtracted in order to focus or generalize the predictive power of the feature-set to ascertain the risk of a medical condition or disease. Presently, the highly selected features, which comprise the feature-sets, are not readily ascertainable in textbooks, conventional databases, online so-called expert diagnostic tools, etc. An example of a simple feature-set or feature-set of a surrogate disease model associated with heart failure comprises and essentially consists of five quantifiable features: (1) ejection fraction; (2) chronicity and (3, 4) acuity of filling pressure; and (5) myocardial relaxation, as shown in FIG. 6.

Figure 3:
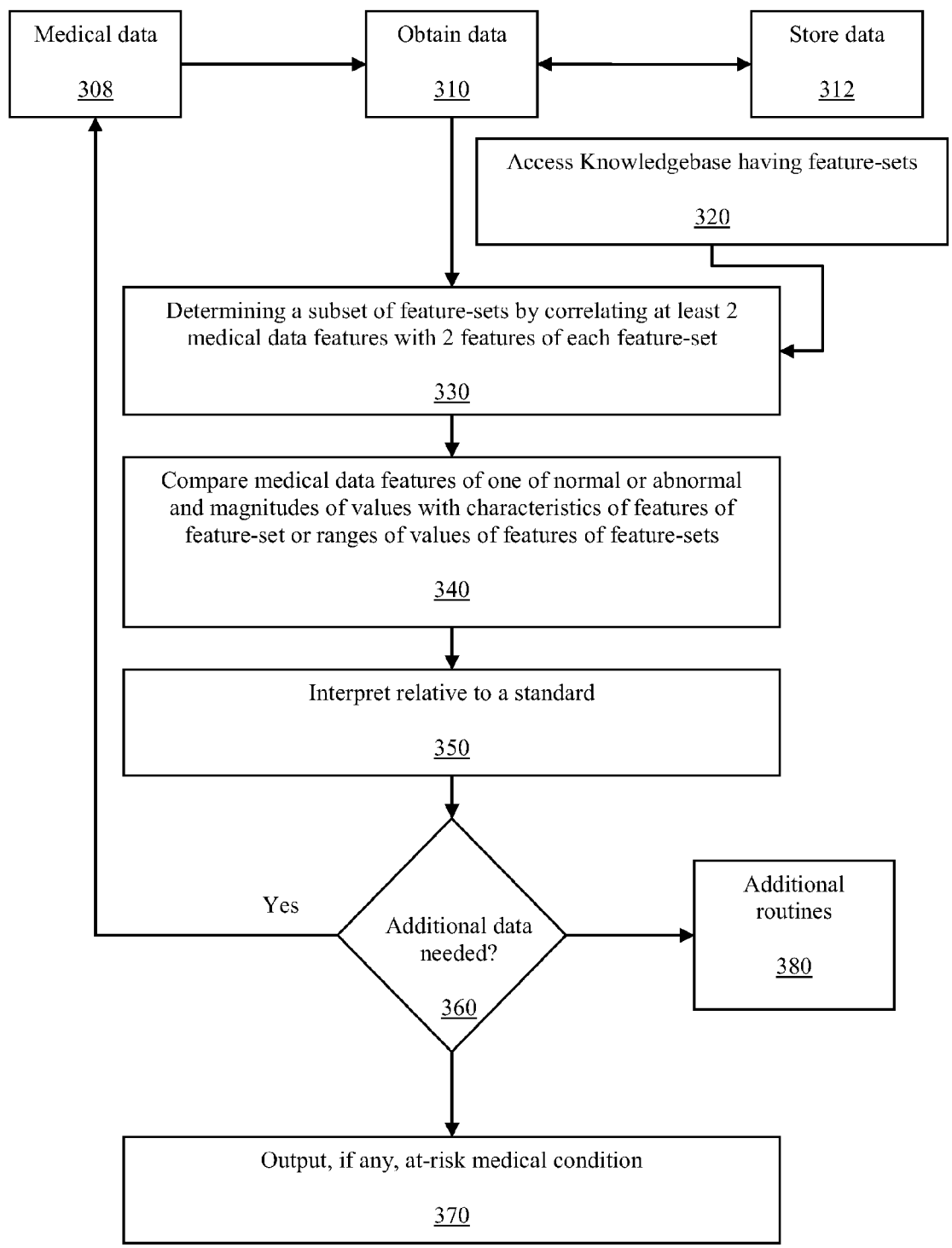
FIGS. 3-5 are flow-charts of the methods by which medical data is analyzed relative to identifying at-risk medical condition, in accordance with an embodiment.

With respect to FIG. 3, a flow chart of the method steps functioning to realize the application of complexity science to medical diagnostics and prevention of disease as described herein is presented. Henceforth, the term medical condition will be used to represent health, normalcy, pre-emergent disease, emerging, or an expressed disease itself. The latter three being at-risk medical conditions. The term medical data is any of various individual items, called features, which relate to at least one of various medical conditions. At least some of the features of the medical data have values. First in step 308, medical data is created and in step 310, medical data is obtained and is input into a processing system and is stored in memory 312. The medical data may be input directly in real time from the apparatus acquiring the data. Examples of medical apparatus that can directly input data into the processing system or memory include but are not limited to x-rays, Echo/Doppler, magnetic resonance (MRI) and other sonography, computer-aided tomography (CAT scans), biochemical laboratory instruments, nuclear devices, genomics, etc. shown as 175 of FIG. 1. Medical data may also be input indirectly such as by the computer system 10 of FIG. 1 accessing stored medical data over a communication connection or a network for a computer storage device using, for instance, an application program interface. A batch data acquisition program may be used to acquire substantial data from a medical institution for an entire day, week, month, etc. Medical data may also be input by a person or entering the data through an input device, such as a keyboard or a microphone, etc.

In step 320, the method described herein access the knowledgebase 140. Recall that the knowledgebase 140 contains a number of feature-sets 160, each representing a general or specific medical condition which may be a disease surrogate or a hub and each having a small number or group of highly-associated features that characterize that particular medical condition. At least some of the highly-associated features have ranges of values. Recall also that this knowledgebase 140 contains validated experts' knowledge of these medical conditions.

The method then identifies those feature-sets, i.e., a subset of all feature-sets that have the highest correlation of features with the input medical data of an individual person in step 330. At least two of the medical data features must correlate with at least two of the highly-associated features of each of the feature-sets in the subset. In this way, the medical data features are transformed from knowledge of the features of the medical data to metadata in the form of the group of highly-associated features of each of the feature-sets in the subset. Based on the input medical data, one or more feature-sets may be identified. A person's medical data may indicate that the person has one or more medical conditions or disease states. Similarly, the medical data may not correlate with any existing feature-set in the knowledgebase 140. In this case, the medical data pertaining to the person may be highlighted for further review by a human expert. Thus, in step 330, the processes and components execute to correlate medical data to features and predict, quantify, and may suggest or monitor treatment for pre-emergent, or emerging or clinically apparent medical conditions and identify possible courses of action.

After appropriate medical data has been input, in steps 340 and 350, associative algorithms 150, appropriate comparisons and expert interpretations are applied to the medical data wherein the magnitudes of the medical data are applied to the features within each selected feature-set to determine a cumulative risk that a person whose medical data is analyzed has or does not have a medical condition of the selected feature-sets. With respect to step 340, it is noted that medical data features can be normal or abnormal or can have magnitudes of values. In a situation where a characteristic is normal or abnormal, such language can pertain to a characteristic like sex where a particular feature-set pertains to a male, as opposed to a female, so that "male" is normal, while "female" would be abnormal for such characteristic. In step 340, a comparison of the medical data features which are one or normal or abnormal magnitudes of values is made to the features of the particular feature-set with respect to whether a feature is normal or abnormal or the magnitude of a value of a feature of the medical data is within the range of values of a feature of the feature-set. The degree of comparison or position of values within ranges which is also a comparison is then measured or interpreted relative to a standard. In this way, an at-risk medical condition of the person can be identified.

When principally directed to the physician or care giver, the process steps described herein further include a step 360 that suggests additional diagnostic tests or evaluations, such as a Further Diagnostic help component 152 in FIG. 1 to assist the data collector in evaluating feature-sets and features that are required to identify possible medical conditions. The medical data may be ambiguous and inconclusive to confidently identify one or more feature-sets. As mentioned above, one or more medical conditions may have been identified, or it is possible that no medical conditions were identified. These situations may arise, for example, when a conclusive identification of a feature-set and hence a medical diagnosis requires, for example, five features but the medical data includes less than five features, or the magnitude of the values are indeterminate. Each feature-set in the knowledgebase 140 has an associated confidence factor for the selection of the feature-set based on the values of the input medical data. If certain features are contradictory or otherwise do not make sense, such as for example the same person having inconsistent laboratory tests, or when a confidence level is too low, a statement that certain data must be confirmed, repeated, excluded, corrected, etc. or that additional medical data is required will be included with the results.

The application of complexity science as in the present method to identify and predict the risk or a likelihood of a disease state is incredibly more powerful than presenting the same input medical data to an "expert." When the same input medical data is given to an "expert" and is input to this method and computerized system for automated management of medical data using expert knowledge and applied complexity science for risk assessment and diagnoses, as described herein, the human "expert" is consistently unpredictable while the automated system herein is consistently predictable. Even when human experts know the features of a feature-set and access the input medical data pertaining to that feature-set, humans do not predict the risk burden of the medical condition as consistently and as quickly as the automated system described herein.

In step 370, based on the comparison of step 340 and the interpretation relative to a standard in step 350, if no additional data is needed as considered in step 360, then if an at-risk medical condition is present, it is identified and output.

In a further embodiment, the results may be output to an application program interface or a user interface in an appropriate format whereby a medical practitioner can read which medical conditions, if any, are predominant and to what degree they exist in a particular patient, i.e., what is the risk of a patient having that medical condition. Additional medical tests or further evaluations may be recommended and included in the output to assist in additional and/or more accurate diagnoses. It is contemplated herein that the output also includes possible treatment options and recommendations based on the magnitude of the risk or expression of the medical condition in the patient.

Figure 4:
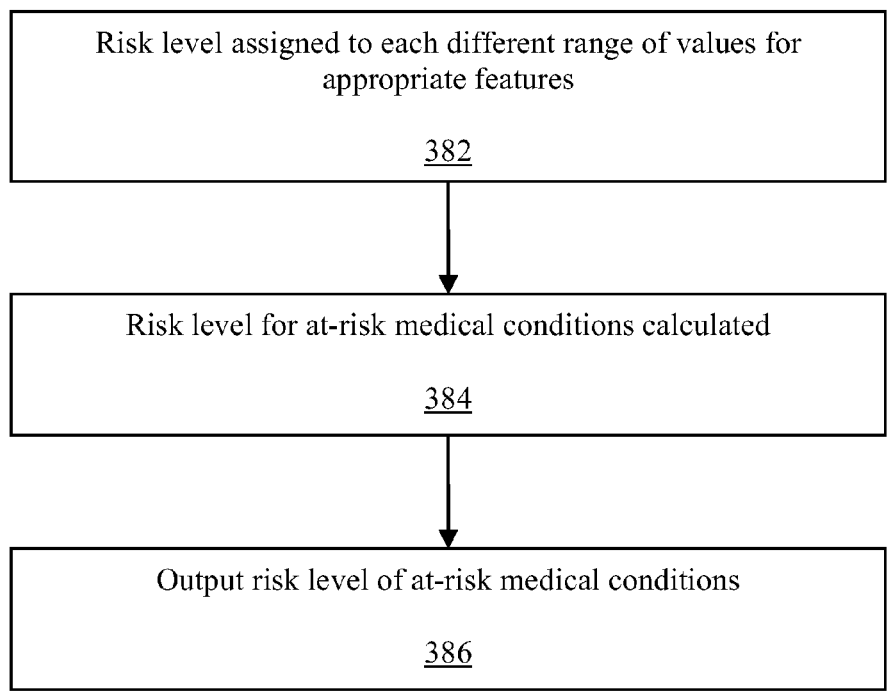
Figure 5:
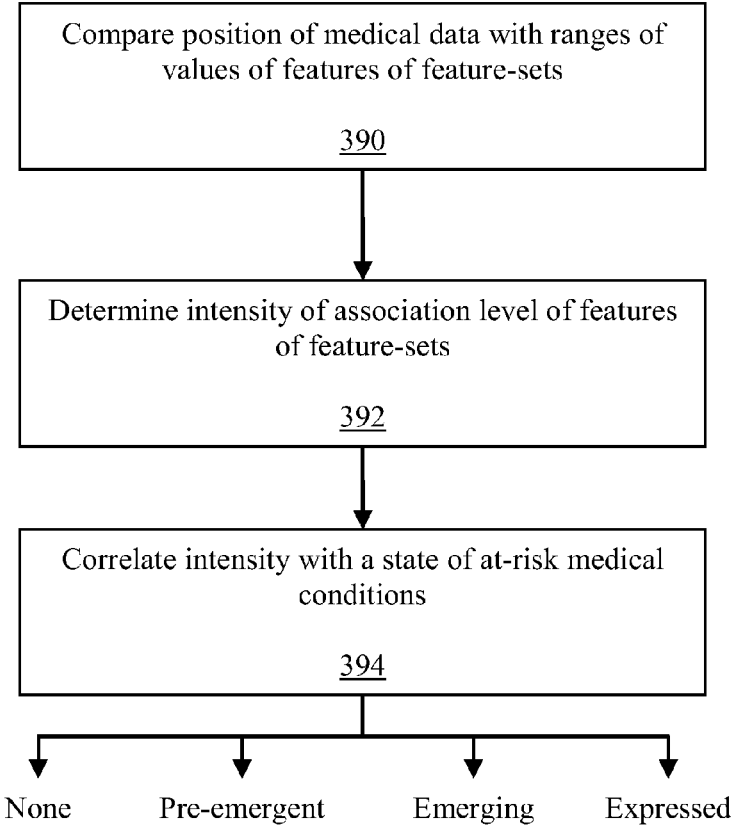

As indicated at step 380, additional routines or embodiments are contemplated as a part of this method. FIGS. 4 and 5 are additional methods leading to an output risk level of an at-risk medical condition and a state of an at-risk medical condition, respectively. With respect to FIG. 4, as shown at step 382, a risk level is assigned to each different range of values for appropriate features of a feature-set. Depending on the magnitudes of values of the medical data, risk levels attach to the data with respect to the highly-associated features of a feature-set. The risk levels of the highly-associated features of a feature-set are assessed relative to an appropriate standard and a risk level for an at-risk medical condition is calculated or obtained at step 384. As shown at step 386, the risk level of the at-risk medical condition is output.

With respect to FIG. 5, positions of the magnitudes of values of the medical data are compared with the ranges of values of the highly-associated features of feature-sets 390. The intensity of association level of the highly-associated features is obtained based on a standard with respect to the positions 392. The intensity of the association level of the highly-associated features is then correlated with a state of at-risk medical conditions 394, particularly, none or normal, pre-emergent, emerging, and expressed.

It is clear from FIGS. 1 and 3, that the method of FIG. 3 is readily embodied in the various configurations of a computer system as shown in FIG. 1. A computer system comprises a central processing unit 112 coupled to a memory 114 such that the central processing unit is programmed to evaluate medical data to identify an at-risk medical condition for a person. The computer system obtains the medical data wherein the medical data has features of at least one of various medical conditions with some of the features having values. A medical knowledge base 140 is accessed from memory 114 and has a plurality of feature-sets relating to the various medical conditions. Each of the feature-sets has a group of highly-associated features relating to particular ones of the various medical conditions with at least some of the highly-associated features having ranges of values. A risk level can be assigned to each different range of values. The central processing unit determines a subset of the plurality of feature-sets by correlating at least two of the features of the medical data with at least two of the highly-associated features of each of the feature-sets in the subset. In this way, knowledge of the features of the medical data is transformed to metadata in the form of the group of transformed highly-associated features of each of the feature-sets in the subset. The central processing unit goes on to compare whether the features of the medical data are one of normal or abnormal and magnitudes of values of the medical data are within the ranges of values of the transformed highly-associated features which are normal or abnormal. A standard is used relative to the comparison so as to identify any at-risk medical conditions of the person. The computer system outputs from an appropriate interface information relating to the at-risk medical condition. The central processing unit may be further programmed to identify an intensity of association levels of the transformed highly-associated features of the feature-sets with a state of the at-risk medical condition based on the magnitude of the values of the features of the medical data wherein the state is either that the person is normal, or has a pre-emergent, emerging, or expressed medical condition or disease.

The methods of FIGS. 3-5 can also be embodied in a non-transitory computer-readable storage medium usable with respect to a computer system of FIG. 1. The storage medium has an executable program stored thereon. The program instructs the central processing unit coupled to the memory and a data-receiving interface to perform steps in accordance with the methods of FIGS. 3-5. In particular, medical data is obtained wherein the data has features of at least one of various medical conditions. At least some of the features of the medical data have values. The medical knowledge base stored in the memory has a plurality of feature-sets relating to the various medical conditions. Each of the plurality of the feature-sets has a group of highly-associated features relating to the particular ones of the various medical conditions. At least some of the highly-associated features have ranges of values. A subset of the plurality of feature-sets is determined by correlating at least two of medical data with at least two of the highly-associated features of each of the feature-sets in the subset. In this way, knowledge of the features of the medical data is transformed to metadata in the form of the group of transformed highly-associated features of each of the feature-sets in the subset. Features of the medical data which are either normal or abnormal or have magnitudes of values are compared with the characteristics of the highly-associated features of the feature-sets in the subset with respect to normality and ranges of values. The comparison is interpreted relative to a standard so as to identify any at-risk medical condition of the person. The programming provides for information relating to the at-risk medical condition, if present, to be outputted from an interface. A risk level can be assigned for the various different ranges of values of a feature in a feature-set. There can be a step of identifying an intensity of association level of the transformed highly-associated features of the feature-sets with a state of the at-risk medical condition based on the magnitude of the values of the features of the medical data.

The application of complexity science to medical diagnoses and prevention of disease as provided and described herein: (1) is capable of quantifying a large set of features; (2) provides a superior test for determining function; (3) quantifies physiologic and anatomic remodeling, (4) reclassifies disease; (5) decreases misclassification; (6) capitalizes on available technology and (7) is a cost-effective means of producing a multivariable biomarker model, i.e., surrogate disease models.

FIG. 6 is an example of the features that may be included in a feature-set identifying and evaluating the risk of heart failure. Within the expert knowledgebase 140, the "heart failure" feature-set has a small group of highly associated features—myocardial relaxation, filling pressure and ejection fraction. No single one of these features is sufficient to characterize the risk of a pre-emergent, emerging or an existing disease state such as heart failure, atrial fibrillation, stroke, etc. A feature-set of a small set of strongly associated features derived from Echo/Doppler cardiography presents six quantifiable features that characterize cardiovascular disease. LAV index (chronicity of filling pressure) and myocardial relaxation are highly associated features. Resting EF, filling pressure, and LV mass are less connected (variable) features. SBP (systolic blood pressure) is a ubiquitous feature.

FIGS. 7-10 present additional feature-sets 160. Each line is a different feature-set of a different medical condition and the features of its feature-set are presented as columns in the table. The feature set for each medical condition is different. At the intersection of the feature (the column) and the feature-set (the line) is the corresponding magnitude of the feature associated with the feature-set of its respective medical condition which represents the variable severity. Clinical correlations enhance the diagnostic specificity such as the feature set of an athletic heart having a benign volume overload but chronic anemia, chronic disease, hyperthyroidism, and other medical conditions presenting a benign volume overload. To distinguish between hypertension and an athletic heart and chronic anemia, for instance, the hypertension feature-set also includes pulse pressure and central aortic pressure and diastolic pressure. A cardiology expert has determined that these features are the minimal number and are the most strongly associated with each other to characterize the medical condition, i.e., each line in the table represents a "hub" and each column in that line represents those actual numeric medical data that not only characterize a medical condition but are also most-influenced by or most highly associated with each other. Thus, in step 330 of FIG. 3, the input medical data is first read to determine what features, if any, are in the input medical data. Based on the features within the input medical data, one or more feature-sets of its respective medical condition are selected. Then in steps 340 and 350, the associative algorithms or standards act upon the magnitudes of the features to determine the feature-set and the associated risk burden, i.e., the state of the medical condition specified by the selected feature-set.

FIGS. 6-9 are feature-sets of different cardiac medical conditions. FIG. 10 provides the features characterizing several metabolic medical conditions. For instance, in FIG. 3, the features associated with diagnosing many cardiac medical conditions are the ejection fraction, EF, the filling pressure and velocity, the myocardial relaxation velocity, and the left atrial volume index, all obtained from echocardiography and various Doppler measurement techniques. These figures are intended to be representative of features that could be considered when constructing the feature-sets in the knowledge base. How the magnitudes of the features, i.e., ABN means abnormal, NL is normal, VAR is variable, etc., are used to assign a risk burden of the medical condition will be considered below. It is contemplated herein that these feature-sets be accessible as a relational database, a nonrelational database, or as objects in an object-oriented database, in a meaningful and connected data relationship. Access to these feature-sets, however, is not limited as stated above but it is further contemplated that other access techniques can also be used and developed.

Below is a chart of some of the features used in the feature-sets of FIGS. 6-10. In the first column is the feature that is closely associated with another feature in characterizing a medical condition. In the second column are the magnitudes or the range of magnitudes of the medical data and in the third column is an assigned risk value to a particular range of magnitudes of the medical data used by the associative algorithms 150 to determine the risk of the medical condition in an individual having these particular medical data. It is preferred that these medical data be directly obtained from instrumentation, for instance, the deceleration time and the ratio of E/A may be directly obtained from pulsed-wave Doppler echocardiography and myocardial relaxation velocity e' may be obtained using tissue Doppler imaging, and then input into the computer system 10 for diagnosis and risk of a medical condition. These features, their magnitudes and the instrumentation used to obtain the medical data are presented by way of example only. A living knowledgebase would contain numerous validated features. It is contemplated throughout that as the knowledgebase 140 grows and becomes more refined that any one of the features, their magnitudes, and the risk assignation of the magnitudes will change as well as the technology used to obtain the raw medical data.

| FEATURE | MEDICAL DATA | RISK VALUE |
|---|---|---|
| Age | ≥75 years | 3 |
|  | 45-74 years | 2 |
|  | 16-44 years | 1 |
|  | Fetal | 2 |
|  | Infant | 2 |
| Body mass index | 18.5-24.9 | 0 |
|  | 25-30 | 1 |
|  | 30-35 | 2 |
|  | >35 | 3 |
| Systolic blood pressure | <120 mm Hg | 0 |
|  | 120-139 mm Hg | 1 |
|  | 140-159 mm Hg | 2 |
|  | ≥160 mm Hg | 3 |
| Diastolic blood pressure | 60-90 mmHg | 0 |
|  | >90 mm Hg | 2 |
|  | <60 mm Hg | 3 |
| Pulse pressure | <55 mm Hg | 0 |
|  | 55-<65 mm Hg | 1 |
|  | 65-80 mm Hg | 2 |
|  | >80 mm Hg | 3 |
| Systolic ejection fraction (EF) | ≥55% | 0 |
|  | 45-54% | 1 |
|  | 31-44% | 2 |
|  | ≤30% | 3 |
| Cardiac index | ≥2.5 | 0 |
|  | 2.0-2.4 | Not use |
|  | <2.0 | 3 |
| Ascending aorta | <25 mm | 0 |
|  | 25-29 mm | 1 |
|  | 30-49 mm | 2 |
|  | ≥50 mm | 3 |
| Heart rate | 60-100 bpm | 0 |
|  | <60 bpm | 1 |
|  | >100 bpm | 2 |
| Pulmonary pressure | ≤35 mm Hg | 0 |
|  | 36-50 mm Hg | 1 |
|  | 51-69 mm Hg | 2 |
|  | ≥70 mm Hg | 3 |
| Superior vena cava flow | No respiratory change | 0 |
|  | Respiratory change | 1 |
| Deceleration time | 140-240 ms | 0 |
|  | >240 ms | 1 |
|  | 140-240 ms, if e' < 10 and/or LAVI > 28 | 2 |
|  | <140 ms | 3 |
| Mitral valve early velocity/ atrial contraction - E/A | 0.75-1.5 | 0 |
|  | <0.75 | 1 |
|  | 0.75-1.5, if e' < 10 and/or LAVI > 28 | 2 |
|  | >1.5 | 3 |
| Myocardial relaxation velocity-e' | ≥10 cm/s | 0 |
|  | ≥9-10 cm/s | 1 |
|  | <9->7 cm/s | 2 |
|  | ≤7 cm/s | 3 |
| Left atrial volume index (LAVI) | 22 ± 6 ml/m² | 0 |
|  | >28-34 | 1 |
|  | >34-<40 | 2 |
|  | ≥40 | 3 |
| Pulmonary vein A reversal and atrial contraction (PVAR and A) duration | <30 ms | 0 |
|  | ≥30 ms | 1 |
| Filling Presure (E/e') | 8-14, if e' > 10 | 0 |
|  | ≥8-<11, if e' < 10 | 1 |
|  | ≥11-<15, if e' < 10 | 2 |
|  | ≥15, if e' < 10 | 3 |

In the table above, the risk value is associated with the magnitudes of the medical data, such as a person older than 75 years is given a risk value of 3 and so on. An associative algorithm then could be the sum of the actual risk values of the features based on the magnitudes of the medical data divided by the sum of the risk values of the features based on the maximum possible values. For instance, the medical data from echocardiography of a patient is: ejection fraction (EF) of 51 percent, filling pressure (E/e') of 12 mm Hg, myocardial relaxation velocity (e') is 8.5 cm/s, and left atrial volume index (LAVI) is 29 ml/m². The 51 percent systolic ejection fraction EF has a risk value of 1 out of a maximum risk value of 3 wherein a risk value of 0 is given when the medical data is in the normal range. The 12 mm Hg filling pressure E/e' of the patient has a risk value of 2 wherein the maximum risk value is a value of 3 and the risk value of 0 when the medical data is within a normal range. Medical data of 8.5 cm/s for myocardial relaxation velocity e' has a risk value 2 wherein the maximum risk may be arbitrarily assigned a risk value 3 and when the medical data is within the normal range, the risk value is 0. The left atrial volume index of 29 ml/m² has a risk value of 1 out of a possible maximum risk value of 3 and a minimum risk value of 0 when the medical data is within the normal range. Applying the example of an associative algorithm given above, the risk that the individual above has a systolic dysfunction is: $(1+2+2+1)/(3+3+3+3)=0.5$. For some features, for example, Cardiac index in the table above, a measurement of 2.0-2.4 would result in a "Not use" score such that the feature would not be used in the risk measurement. Output from the method and the components herein would indicate that the individual has an increased risk of systolic dysfunction, diastolic dysfunction, secondary atrial fibrillation, atrial pressure overload, and several other cardiac medical conditions, which medical condition(s) may be in the preemergent stage. For additional diagnoses of secondary pulmonary hypertension, primary pulmonary hypertension, mixed pulmonary hypertension, the output of the method and components herein would either read or request input medical data for the features of pulmonary artery pressure and superior vena cava flow, or for hypertensive heart disease, acquire or request input medical data of blood pressure and left ventricle mass.

The methods and components herein as described then receive and store the medical data comprising the magnitudes of the features. Automatically, the methods and components will determine the most pertinent features ascribable to a feature-set of a medical condition. Assessment of the state of the medical condition means evaluating the risk that the medical data indicates whether a person has a pre-emergent medical condition, emerging, or an expressed medical condition, or if treatment is ongoing, whether the treatment is effective. This assessment is accomplished using associative algorithms 150, one example of which is presented below. One of skill in the art will realize that just as the feature-sets change and become refined, so also will associative algorithms 150, and that there are other associative algorithms 150 that can be applied to the medical data. For instance, a simple numerical counting and averaging method can be replaced by a more sophisticated probability statistical method, or other higher-order nonlinear evaluation methods. It is further contemplated that more than one associative algorithm 150 be used, i.e., one medical condition, e.g., ovarian cancer, may use a simpler or a more complicated associative algorithm 150 than a different medical condition, e.g., heart disease. The associative algorithms 150, moreover, are self-learning and self-correcting so that as more and more medical data is input and as the knowledgebase 140 changes and corrects, the associative algorithms 150 can respond and can converge or correct itself to attain a higher rate of prediction and diagnoses.

In a basic sense, a knowledge base 140 is created by adding or modifying a candidate feature-set relating to a medical condition. In a first step, at least one candidate feature is considered relative to the rest of the feature-set. In this regard, the candidate feature-set has at least one other existing feature. A comparison of the at least one candidate feature is made with the at least one other existing feature. The at least one candidate feature is elected for inclusion in the candidate feature-set if when the candidate feature is abnormal or within a range of values which are abnormal there is a correlative or associative effect with the other existing features such that together they have an increased association with each other and with the medical condition to which the features and feature-set relate.

Applying the knowledgebase 140 to medical data and then using associative algorithms 150 for determining the relationship between features and the medical data, health care providers are now able to bridge the chasm between complex top-down clinical and bottom-up reductionist modeling. The automated methods and systems as described herein are used to predict, quantify, and prevent any medical condition associated with a feature-set. To evaluate the efficacy of treatment, a patient can provide medical input data at different times during a treatment regime and the medical practitioner can determine if the medical condition or disease is responding to the treatment and to what degree. The embodiments described herein thus provide a very robust means of predicting the emergence of preclinical disease, quantifying the extent of the medical condition or disease, recommending measures to prevent the disease, and evaluating the effectiveness of treatment of a medical condition.

What is claimed is:

1. A method for evaluating medical data of an individual to identify, if any, at-risk medical conditions, comprising:
    accessing from a memory a medical knowledgebase having a plurality of feature-sets relating to various medical conditions, each of the plurality of feature-sets having a group of highly-associated features relating to the various medical conditions, at least some of said highly-associated features having a plurality of ranges of values, wherein a risk level is assigned for each of the plurality of ranges of values, and wherein the risk level is calculated with a computer for each of the plurality of ranges of values based on associative algorithms acting upon magnitudes of the plurality of ranges of values of the at least some of said highly-associated features within the medical knowledgebase;
    obtaining with the computer the medical data of the individual, the medical data having comprising features of at least one of the various medical conditions, wherein at least some of the features of the medical data of the individual having values;
    identifying with the computer a subset of the plurality of feature-sets in the medical knowledgebase that correlates with the obtained medical data of the individual by correlating at least two of the features of the medical data of the individual with at least two of said highly-associated features of each of the feature-sets in the subset thereby transforming knowledge of the features of the medical data of the individual to metadata in the form of the group of transformed highly-associated features of each of the feature-sets in the subset;
    determining with the computer whether the features of the medical data of the individual are one of normal or abnormal and whether the values of the medical data of the individual are within the magnitudes of the ranges of values of the transformed highly-associated features which are normal or abnormal to interpret relative to a standard as to identify, if any, at-risk medical conditions of said individual;
    assigning at least one risk level to the medical data of the individual based on the determination; and
    outputting from the computer information relating to, if any, the at-risk medical conditions.

2. The method of claim 1, including outputting from the computer a request to acquire additional medical data to further assess the at-risk medical conditions.

3. The method of claim 1, including further comprising identifying an intensity of association levels of the transformed highly-associated features of the feature-sets with a state of the at-risk medical conditions, the state of the at-risk medical conditions being based on a magnitude of aggregated values of the features of the medical data of the individual, said state being one of: none, pre-emergent, emerging, and expressed.

4. The method of claim 1, wherein the at risk-medical condition is identified from at least two highly-associated features for a particular one of said feature-sets in the subset.

5. A computer system for evaluating medical data of an individual to identify an at-risk medical condition, said computer system comprising a central processing unit coupled to a memory, said central processing unit being programmed to:

access from the memory a medical knowledgebase having a plurality of feature-sets relating to various medical conditions, each of the plurality of feature-sets having a group of highly-associated features relating to the various medical conditions, at least some of said highly-associated features having a plurality of ranges of values, wherein as risk level is assigned for each of the plurality of ranges of values, and wherein the risk level is calculated by the central processing unit for each of the plurality of ranges of values based on associative algorithms acting upon magnitudes of the plurality of ranges of values of the at least some of said highly-associated features within the medical knowledgebase;

obtain the medical data of the individual comprising features of at least one of the various medical conditions, wherein at least some of the features of the medical data of the individual having values;

identify a subset of the plurality of feature-sets in the medical knowledgebase that correlates with the obtained medical data of the individual by correlating at least two of the features of the medical data of the individual with at least two of said highly-associated features of each of the feature-sets in the subset thereby transforming knowledge of the features of the medical data of the individual to metadata in the of the group of transformed highly-associated features of each of the feature-sets in the subset;

determine whether the features of the medical data of the individual are one of normal or abnormal and whether the values of the medical data of the individual are within the magnitudes of the ranges of values of the transformed highly-associated features which are normal or abnormal to interpret relative to a standard as to identify, if any, at-risk medical conditions of said individual;

assign at least one risk level to the medical data of the individual based on the determination; and output from an interface information relating to, if any, the at-risk medical conditions.

6. The computer system of claim 5, wherein said central processing unit being further programmed to identify an intensity of association levels of the transformed highly-associated features of the feature-sets with a state of the at-risk medical conditions, the state of the at-risk medical conditions being based on a magnitude of aggregated values of the features of the medical data of the individual, said state being one of: none, pre-emergent, emerging, and expressed.

7. A non-transitory computer-readable storage medium with an executable program stored thereon, said program evaluating medical data of an individual, said medium located on a computer system wherein said program instructs a central processing unit coupled to a memory and to a data receiving interface to perform the following steps:

access from the memory a medical knowledgebase having a plurality of feature-sets relating to various medical conditions, each of the plurality of feature-sets having a group of highly-associated features relating to the various medical conditions, at least some of said highly-associated features having a plurality of ranges of values, wherein a risk level is assigned for each of the plurality of ranges of values, and wherein the risk level is calculated by the central processing unit for each of the plurality of ranges of values based on associative algorithms acting upon magnitudes of the plurality of ranges of values of the at least some of said highly-associated features within the medical knowledgebase;

obtain the medical data of the individual, said medical data having features of at least one of the various medical conditions, wherein at least some of the features of the medical data of the individual having values;

identify a subset of the plurality of feature-sets in the medical knowledgebase that correlates with the obtained medical data of the individual by correlating at least two of the features of the medical data of the individual with at least two of said highly-associated features of each of the feature-sets in the subset thereby transforming knowledge of the features of the medical data of the individual to metadata in the form of the group of transformed highly-associated features of each of the feature-sets in the subset;

determine whether the features of the medical data of the individual are one of normal or abnormal and whether the values of the medical data of the individual are within the magnitudes of the ranges of values of the transformed highly-associated features which are normal or abnormal to interpret relative to a standard as to identify, if any, at-risk medical conditions of said individual;

assign at least one risk level to the medical data of said individual based on the determination; and output from interface information relating to the at-risk medical conditions.

8. The storage medium of claim 7, wherein said program includes a further step of identifying an intensity of association levels of the transformed highly-associated features of the feature-sets with a state of the at-risk medical conditions, the state of the at-risk medical conditions being based on a magnitude of aggregated values of the features of the medical data of the individual, said state being one of: none, pre-emergent, emerging, and expressed.

9. The method of claim 1, further comprising adding or modifying a candidate feature-set relating to a specific medical condition in the medical knowledgebase, wherein adding or modifying a candidate feature-set comprises:

inputting into the computer at least one candidate feature to be considered relative to the candidate feature-set, said candidate feature-set having at least one other existing feature;

comparing, with the computer, the at least one candidate feature with the at least one other existing feature of the candidate feature-set;

selecting the at least one candidate feature for inclusion in the candidate feature-set if when the at least one candidate feature is one of abnormal and within a range of values that is abnormal, there is a correlative effect with the at least one other existing feature such that together the at least one candidate feature and the at least one other existing feature have an increased association level with the specific medical condition to which the candidate feature-set relates; and including the candidate feature-set in the medical knowledgebase.

* * * * *

UNITED STATES PATENT AND TRADEMARK OFFICE
CERTIFICATE OF CORRECTION

| | | |
|---|---|---|
| PATENT NO. | : 8,554,580 B2 | Page 1 of 1 |
| APPLICATION NO. | : 12/578325 | |
| DATED | : October 8, 2013 | |
| INVENTOR(S) | : Seward | |

It is certified that error appears in the above-identified patent and that said Letters Patent is hereby corrected as shown below:

On the Title Page, Item (56), under "FOREIGN PATENT DOCUMENTS", in Column 2, Line 2, delete "2002-059099" and insert -- 2002-056099 --, therefor.

In the Specification:

In Column 13, Line 51, delete "feature-sets 150," and insert -- feature-sets 160, --, therefor.

In Column 13, Line 52, delete "feature-set 150" and insert -- feature-set 160 --, therefor.

In Column 20, in Table, under "MEDICAL DATA", Line 34, delete "$\geq$9-10 cm/s" and insert -- $\geq$9-<10 cm/s --, therefor.

In Column 20, in Table, under "FEATURE", Line 15, delete "Presure" and insert -- Pressure --, therefor.

In the Claims:

In Column 23, Line 11, in Claim 5, delete "wherein as" and insert -- wherein a --, therefor.

In Column 23, Line 29, in Claim 5, delete "the of" and insert -- the form of --, therefor.

Signed and Sealed this
Eleventh Day of February, 2014

Michelle K. Lee
*Deputy Director of the United States Patent and Trademark Office*